US008215313B1

(12) United States Patent
Waltz

(10) Patent No.: US 8,215,313 B1
(45) Date of Patent: Jul. 10, 2012

(54) MEDICAL GARMENT SYSTEMS

(76) Inventor: Lisa R. Waltz, Peoria, AZ (US)

(*) Notice: Subject to any disclaimer, the term of this patent is extended or adjusted under 35 U.S.C. 154(b) by 165 days.

(21) Appl. No.: 12/509,378

(22) Filed: Jul. 24, 2009

Related U.S. Application Data

(60) Provisional application No. 61/090,868, filed on Aug. 21, 2008, provisional application No. 61/085,779, filed on Aug. 1, 2008.

(51) Int. Cl.
*A61F 5/37* (2006.01)
*A61B 19/00* (2006.01)

(52) U.S. Cl. ......... 128/873; 128/874; 128/869; 128/849

(58) Field of Classification Search ............ 128/849, 128/853, 872–874, 878, 882, 877, 869; 2/114, 2/309; 5/600, 601; 119/725, 814, 816
See application file for complete search history.

(56) References Cited

U.S. PATENT DOCUMENTS

| | | | | |
|---|---|---|---|---|
| 826,648 A * | 7/1906 | Challenger | | 128/876 |
| 1,183,225 A * | 5/1916 | Overmeyer | | 128/878 |
| 1,219,453 A * | 3/1917 | Hansen | | 128/878 |
| 2,766,751 A * | 10/1956 | Topa | | 128/870 |
| 2,940,443 A * | 6/1960 | Baker | | 128/874 |
| 2,948,278 A * | 8/1960 | Topa | | 128/873 |
| 3,315,671 A * | 4/1967 | Creelman | | 128/870 |
| 3,986,505 A * | 10/1976 | Power | | 128/846 |
| 4,026,282 A | 5/1977 | Thomas | | |
| 4,484,571 A * | 11/1984 | Velazquez | | 5/601 |
| 4,488,544 A | 12/1984 | Triunfol | | |
| 4,550,724 A * | 11/1985 | Berrehail | | 128/874 |
| 4,683,594 A | 8/1987 | Feinberg | | |
| 4,685,454 A | 8/1987 | Posey | | |
| 4,742,821 A * | 5/1988 | Wootan | | 128/873 |
| 4,744,354 A | 5/1988 | Triunfol | | |
| 4,852,587 A * | 8/1989 | Share | | 128/869 |
| 4,858,625 A * | 8/1989 | Cramer | | 128/872 |
| 5,048,122 A | 9/1991 | Prieur | | |
| 5,084,914 A | 2/1992 | Hesch | | |
| 5,267,352 A | 12/1993 | Rodarmel | | |
| 5,392,786 A * | 2/1995 | Lewis et al. | | 128/877 |
| 5,549,121 A * | 8/1996 | Vinci | | 128/878 |
| 5,652,962 A | 8/1997 | Patnode | | |
| 5,727,255 A | 3/1998 | Minks | | |
| 5,806,096 A | 9/1998 | Pennington | | |
| 5,887,279 A | 3/1999 | Elting et al. | | |
| 6,024,091 A | 2/2000 | Bennett | | |
| 6,393,612 B1 * | 5/2002 | Thach et al. | | 2/69.5 |
| 6,450,168 B1 * | 9/2002 | Nguyen | | 128/869 |
| 6,694,521 B1 | 2/2004 | Hopkins | | |
| 7,073,204 B1 * | 7/2006 | Boyles | | 2/114 |
| 7,143,449 B2 | 12/2006 | Young | | |
| 7,533,673 B2 * | 5/2009 | Lewis et al. | | 128/849 |

FOREIGN PATENT DOCUMENTS

WO W002082976 A2 10/2002

* cited by examiner

*Primary Examiner* — Patricia Bianco
*Assistant Examiner* — Kari Petrik
(74) *Attorney, Agent, or Firm* — Stoneman Law Patent Group; Martin L. Stoneman; Eric Fish

(57) ABSTRACT

A medical garment system for comfortably restraining at least one limb of a gown wearer while permitting the wearer to receive medical treatment. The medical garment system is particularly useful for special needs patients, such as autistic children, who may become frightened when medical personnel are attempting to administer medication. Such patients may react by violently moving their arms, causing themselves or the medical personnel harm. When the arms of such a patient are comfortably subdued during such procedures, the patient is better protected from injury.

15 Claims, 3 Drawing Sheets

MEDICAL GARMENT SYSTEMS

CROSS-REFERENCE TO RELATED APPLICATION

The present application is related to and claims priority from prior provisional application Ser. No. 61/085,779, filed Aug. 1, 2008, entitled "MEDICAL GARMENT SYSTEMS", and is also related to and claims priority from prior provisional application Ser. No. 61/090,868, filed Aug. 21, 2008, entitled "MEDICAL GARMENT SYSTEMS", the contents of both of which are incorporated herein by this reference and are not admitted to be prior art with respect to the present invention by the mention in this cross-reference section.

BACKGROUND

This invention relates to providing a system for improved medical garments. More particularly, this invention relates to providing a system for comfortably restraining at least one limb of a gown wearer, while permitting the wearer to receive medical treatment.

Medical garments are used to provide a means for covering and protecting patients and medical personnel. Some special needs patients, such as autistic children, may become frightened when medical personnel are attempting to administer medication. When special needs patients are scared, they may react by violently moving their arms, causing themselves or the medical personnel harm. When the arms of such a patient are comfortably subdued during such procedures, the patient is better protected from injury. When special needs patients are required to be comfortably restrained, one of the designated apparel for such clinical restraint is a straight jacket. The straight jacket does not provide a garment that cooperates with typical medical procedures and treatments, such as, for example, when they involve injections or a need for accessing portions of the restrained torso. Thus, a need for a comfortable restraint exists to permit medical personnel to administer medical treatment to special needs patients while protecting both the patient and medical personnel from harm.

OBJECTS AND FEATURES OF THE INVENTION

A primary object and feature of the present invention is to provide a system overcoming the above-mentioned problems.

It is a further object and feature of the present invention to provide such a system for comfortably restraining a special needs patient.

It is a further object and feature of the present invention to provide such a system that provides a disguised opening for access to the elbow portion of the special needs patient.

It is a further object and feature of the present invention to provide such a system comprising inner restraining sleeves.

It is a further object and feature of the present invention to provide such a system wherein the medical garment wraps around the special needs patient.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a medical garment system, relating to restraining at least one arm adjacent the torso of at least one gown wearer, comprising: at least one torso enclosure, having at least one interior surface and at least one exterior surface, structured and arranged to enclose such torso; wherein such at least one torso enclosure comprises at least one arm restrainer, located adjacent such at least one interior surface, adapted to restrain the at least one arm of the at least one gown wearer; wherein such medical garment system comprises at least one access to access at least one arm portion of the at least one gown wearer; wherein such at least one access comprises such at least one arm restrainer; and wherein such at least one access comprises at least one medical-procedure-permitter structured and arranged to permit medical procedures relating to the at least one gown wearer.

Moreover, it provides such a medical garment system, wherein such at least one torso enclosure comprises at least one hospital gown permitting unrestrained patient mobility in relation to hospital beds. Additionally, it provides such a medical garment system, wherein such arm restrainer is structured and arranged to limit movement of the at least one arm. Also, it provides such a medical garment system, wherein such at least one arm restrainer comprise one right-arm-inner-restraining sleeve and one left-arm-inner-restraining sleeve. In addition, it provides such a medical garment system, wherein such at least one medical-procedure-permitter comprises: at least one first aperture through such at least one arm restrainer; and at least one second aperture through such at least one exterior surface; wherein such at least one first aperture and such at least one second aperture are aligned. And, it provides such a medical garment system, wherein such at least one first aperture and such at least one second aperture are situate along at least one seam of such at least one hospital gown.

Further, it provides such a medical garment system, wherein such at least one first aperture and such at least one second aperture are situate adjacent about the center of such at least one arm restrainer. Even further, it provides such a medical garment system, wherein such at least one right-arm-inner-restraining sleeve and such at least one left-arm-inner-restraining sleeve each further comprise at least one elastic cuff structured and arranged to assist maintaining the at least one arm within such at least one right-arm-inner-restraining sleeve and such at least one left-arm-inner-restraining sleeve when so placed. Moreover, it provides such a medical garment system, wherein such at least one torso enclosure comprises one hospital gown, having one first longitudinal end and one second longitudinal end, structured and arrange to enclose at least the torso of at least one gown wearer.

Additionally, it provides such a medical garment system, wherein such at least one gown further comprises: at least one upper portion, at least one middle portion and at least one bottom portion; and at least one openable closure structured and arranged to assist in opening or closing such one first longitudinal end and one second longitudinal end; wherein when the arms of such gown wearer are placed into a respective such at least one right-arm-inner-restraining sleeve and such at least one left-arm-inner-restraining sleeve and such at least one gown is closed with such at least one openable closure, the arms of the gown wearer are restrained from contact with each other. Also, it provides such a medical garment system, wherein such at least one openable closure comprises: at least four pair of ties, each such pair of ties situate opposite each other, structured and arranged to be tied together; wherein one of such at least four pair of ties is situate on such at least one upper portion of such at least one gown; wherein two of such at least four pair of ties are situate about such at least one middle portion of such at least one gown; and wherein one of such at least four pair of ties is situate on such at least one bottom portion of such at least one gown.

In accordance with another preferred embodiment hereof, this invention provides a medical garment system, relating to restraining at least one arm adjacent the torso of at least one gown wearer, comprising: at least one torso enclosure, having at least one interior surface and at least one exterior surface, structured and arranged to enclose such torso; wherein such at least one torso enclosure comprises at least one arm restrainer, located adjacent such at least one interior surface, adapted to restrain the at least one arm of the at least one gown wearer; wherein such medical garment system comprises at least one access to access at least one arm portion of the at least one gown wearer; wherein such at least one access comprises such at least one arm restrainer; wherein such at least one access comprises at least one medical-procedure-permitter structured and arranged to permit medical procedures relating to the at least one gown wearer; wherein such at least one torso enclosure comprises at least one hospital gown permitting unrestrained patient mobility in relation to hospital beds; wherein such arm restrainer is structured and arranged to limit movement of the at least one arm; wherein such at least one arm restrainer comprise one right-arm-inner-restraining sleeve and one left-arm-inner-restraining sleeve; and wherein such at least one access comprises at least one first aperture through such at least one arm restrainer, and at least one second aperture through such at least one exterior surface, wherein such at least one first aperture and such at least one second aperture are aligned.

In addition, it provides such a medical garment system wherein such at least one first aperture and such at least one second aperture are situate along at least one seam of such at least one hospital gown. And, it provides such a medical garment system wherein such at least one first aperture and such at least one second aperture are situate adjacent about the center of such at least one arm restrainer. Further, it provides such a medical garment system wherein such at least one right-arm-inner-restraining sleeve and such at least one left-arm-inner-restraining sleeve each further comprise at least one elastic cuff structured and arranged to assist maintaining the at least one arm within such at least one right-arm-inner-restraining sleeve and such at least one left-arm-inner-restraining sleeve when so placed.

In accordance with another preferred embodiment hereof, this invention provides a method of administering at least one medical procedure to at least one patient's arm comprising the steps of: providing at least one torso enclosure, having at least one interior surface and at least one exterior surface, structured and arranged to enclose such torso; wherein such at least one torso enclosure comprises at least one arm restrainer, located adjacent such at least one interior surface, adapted to restrain the at least one arm of the at least one gown wearer; wherein such medical garment system comprises at least one access to access at least one arm portion of the at least one gown wearer; wherein such at least one access comprises such at least one arm restrainer; and wherein such at least one access comprises at least one medical-procedure-permitter structured and arranged to permit medical procedures relating to the at least one gown wearer; inserting such at least one patient's arm into such at least one arm restrainer; closing such hospital gown so as to restrain arm movement of such patient while administering such at least one medical procedure; administering such at least one medical procedure by way of such at least one access.

Even further, it provides such a method of administering, wherein such at least one arm restrainer comprise one right-arm-inner-restraining sleeve and one left-arm-inner-restraining sleeve. Even further, it provides such a method of administering, wherein such at least one right-arm-inner-restraining sleeve and such at least one left-arm-inner-restraining sleeve each further comprise at least one elastic cuff structured and arranged to assist maintaining the at least one arm within such at least one right-arm-inner-restraining sleeve and such at least one left-arm-inner-restraining sleeve when so placed. Even further, it provides such a method of administering, wherein such at least one gown comprises: at least one upper portion, at least one middle portion and at least one bottom portion; and at least one openable closure structured and arranged to assist in opening or closing such at least one gown; wherein when the arms of such gown wearer are placed into a respective such at least one right-arm-inner-restraining sleeve and such at least one left-arm-inner-restraining sleeve and such at least one gown is closed with such at least one openable closure, the arms of the gown wearer are restrained from contact with each other.

In accordance with another preferred embodiment hereof, this invention provides a medical garment system, relating to restraining at least one arm of at least one gown wearer, comprising: torso enclosure means, having at least one interior surface and at least one exterior surface, for enclosing the torso of the at least one gown wearer; wherein such torso enclosure means comprises arm restrainer means, located adjacent such at least one interior surface, for restraining the at least one arm of the at least one gown wearer; wherein such medical garment system comprises access means for accessing at least one arm portion of the at least one gown wearer; wherein such access means comprises such arm restrainer means; and wherein such access means comprises medical-procedure-permitter means for permitting medical procedures relating to the at least one gown wearer.

In accordance with another preferred embodiment hereof, this invention provides each and every novel feature, element, combination, step and/or method disclosed or suggested by this patent application.

DETAILED DESCRIPTION OF THE BEST MODES AND PREFERRED EMBODIMENTS OF THE INVENTION

A preferred embodiment of the present invention relates to a medical garment designed to comfortably restrain at least one limb of a gown wearer, thereby permitting the gown wearer to receive medical treatment by medical personnel. A gown wearer preferably comprises at least special needs patients with physical or mental abnormalities. For example, special needs patients may include autistic persons, persons with brain damage, persons having loss of control of movement, squirmy babies, etc. Medical personnel comprise at least anyone who administers medical treatment to the gown wearer.

When special needs patients, such as users who suffer from autism or brain damage, along with babies that continually squirm and move around, are being medically treated with devices that include shots, IV's, medical patches, or (feeding tubes), they often pull out such devices or strike at the medical personnel. Further, physical methods to limit movement and restrain the gown wearer by medical personnel can harm or excite the patient and make treatment more difficult.

Figure 1:
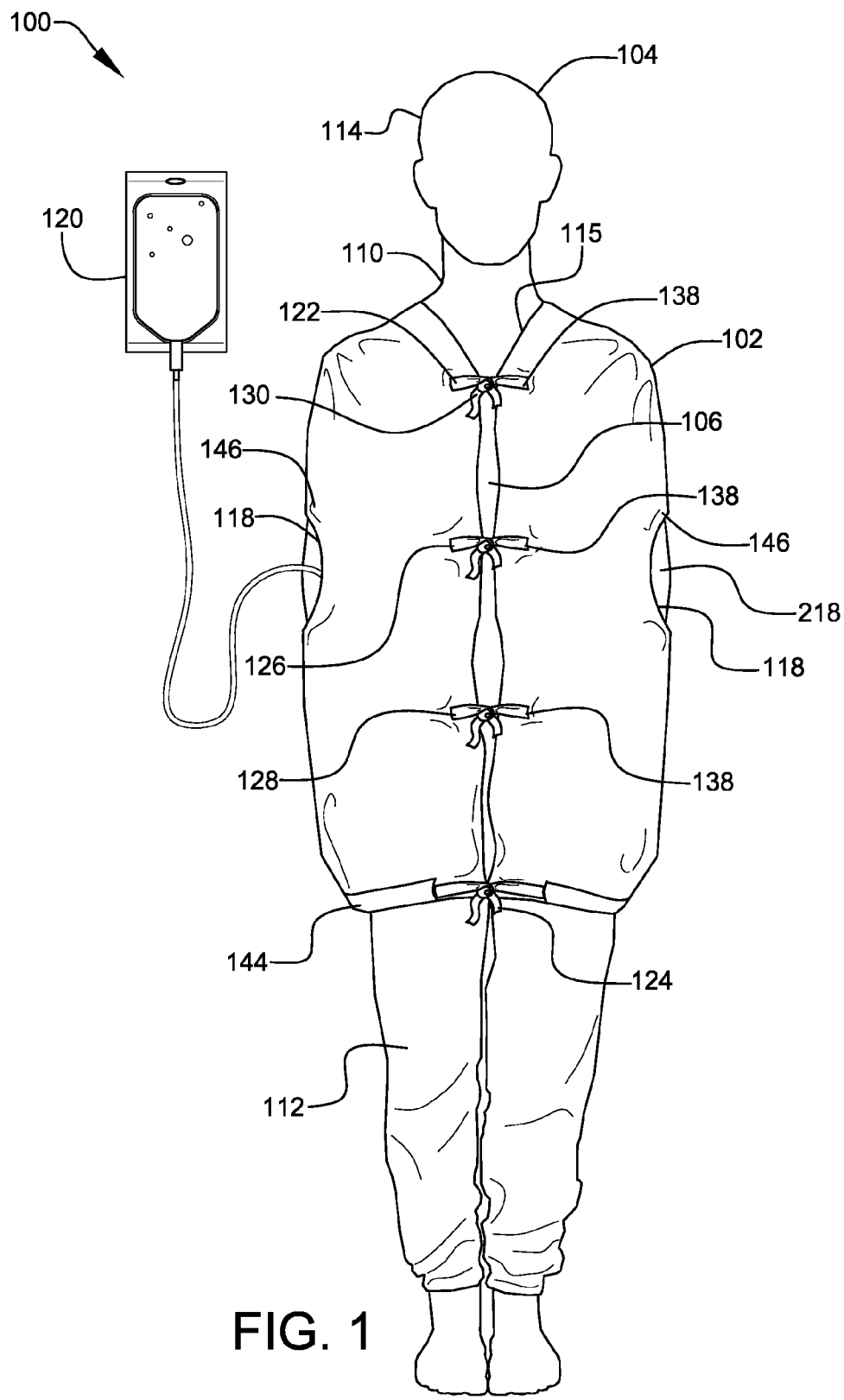
FIG. 1 shows a front perspective view of a medical garment of a medical garment system, illustrating the medical garment supported adjacent a gown wearer, according to a preferred embodiment of the present invention.
Figure 2:
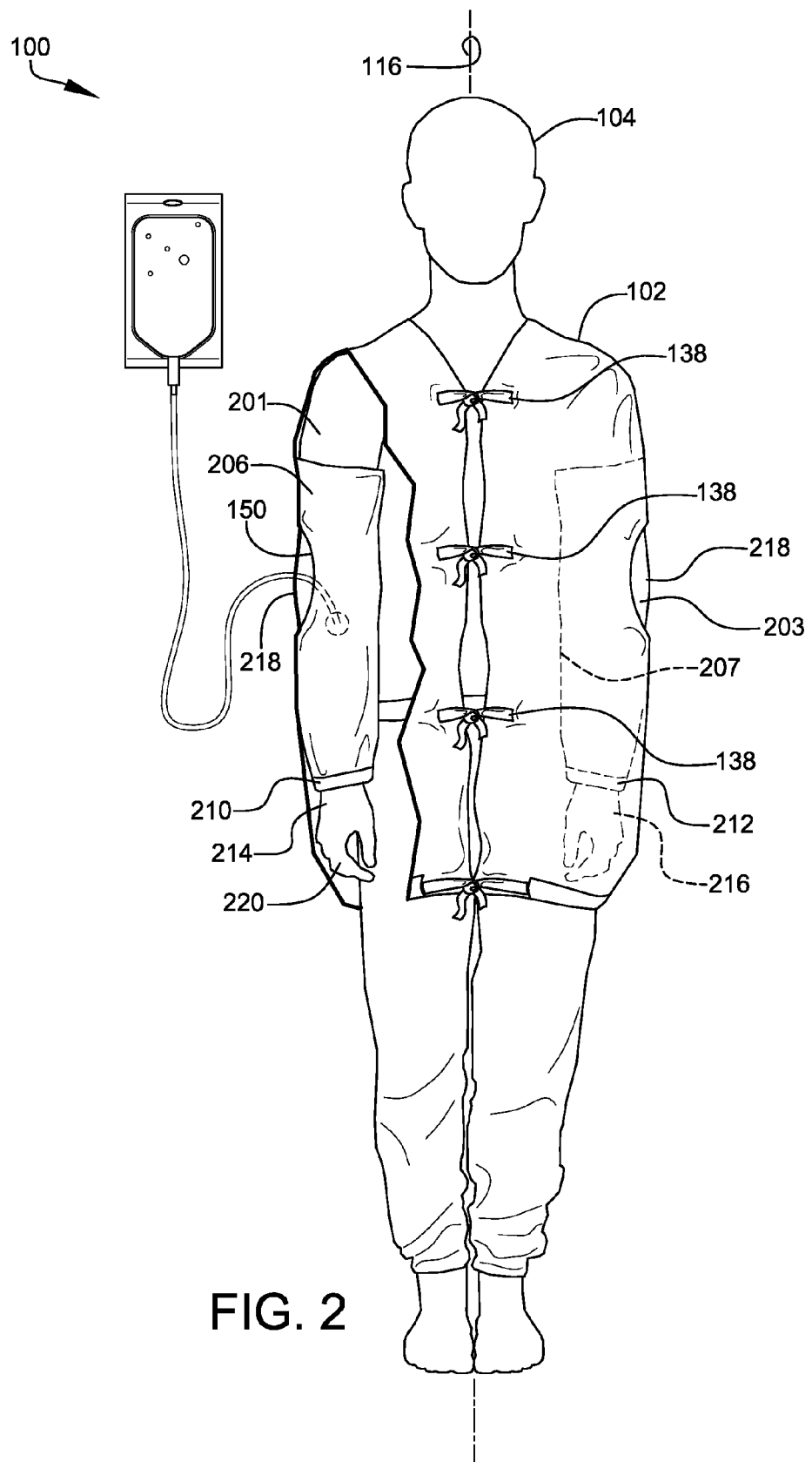
FIG. 2 shows a front cut-away view illustrating a right inner restraining sleeve within the medical garment of the medical garment system, supported adjacent the gown wearer, according to the preferred embodiment of FIG. 1.

FIG. 1 shows a front perspective view of medical garment 102, of medical garment system 100, illustrating medical garment 102 supported adjacent gown wearer 104, according to a preferred embodiment of the present invention. FIG. 2 shows a front cut-away view illustrating right inner restraining sleeve 206 of medical garment 102 of medical garment system 100, supported adjacent gown wearer 104, according to the preferred embodiment of FIG. 1.

Figure 3:
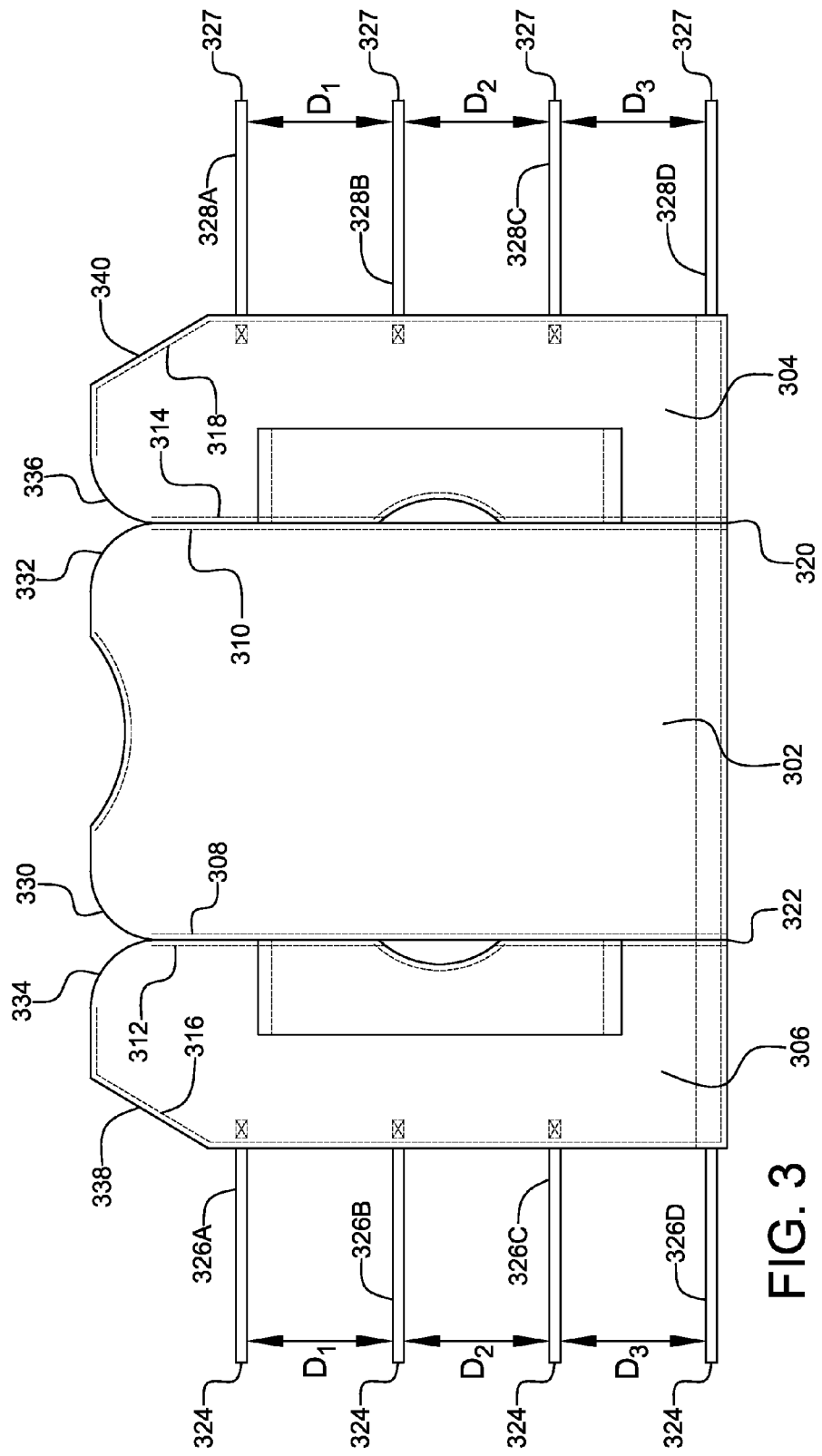
FIG. 3 shows a front perspective view, illustrating the medical garment of the medical garment system unstitched and laid flat, according to the preferred embodiment of the present invention.

Medical garment 102 is preferably adapted to wrap around torso 106 of gown wearer 104 during use, as shown in both FIG. 1 and FIG. 2. When medical garment 102 is wrapped around torso 106 of gown wearer 104 as shown, right arm 201 and left arm 202 are housed inside medical garment 102. Right arm 201 is preferably housed in right inner restraining sleeve 206 and left arm 203 is preferably housed in left inner restraining sleeve 207 (dotted line), as shown. Right inner restraining sleeve 206 and left inner restraining sleeve 207 are preferably attached to the inner side (i.e. adjacent wearer's skin) of the medical garment 102 (at least embodying herein torso enclosure means, having at least one interior surface and at least one exterior surface, for enclosing the torso of the at least one gown wearer), preferably along a stitched seam (best viewed in FIG. 3), as shown. Right inner restraining sleeve 206 and left inner restraining sleeve 207 preferably function to limit movement/motion of each respective right arm 201 and left arm 202 of gown wearer 104, particularly when receiving medical treatment. Preferably, when right arm 201 and left arm 203 are comfortably subdued during such medical procedures, gown wearer 104 is better protected from injury should excessive movement occur. Additionally, right inner restraining sleeve 206 and left inner restraining sleeve 207 (at least embodying herein wherein such torso enclosure means comprises arm restrainer means, located adjacent such at least one interior surface, for restraining the at least one arm of the at least one gown wearer) reduce the likelihood that gown wearer 104 will remove medical devices such as IV's, medical patches, etc.; thus reducing the potential for self-injury or injury to medical personnel. A cut-away view of right inner restraining sleeve 206 is shown in FIG. 3.

Right inner restraining sleeve 206 preferably comprises right elastic cuff 210 preferably adapted to cinch around right wrist portion 214 to preferably prevent the ingress of the wearer's right hand 220 into right inner restraining sleeve 206, as shown. Similarly, although not depicted in the cut-away view of FIG. 2, left inner restraining sleeve 207 preferably comprises a left elastic cuff 212 preferably adapted to cinch around left wrist portion 216 so as to not permit the ingress of the wearer's left hand into left inner restraining sleeve 207.

Preferably, right elastic cuff 210 comprises a width of about 1 inch and is secured to right inner restraining sleeve 206 by stitching. Moreover, preferably, left elastic cuff 212 comprises a width of about 1 inch and is secured to left inner restraining sleeve 207 by stitching. Upon reading this specification, those with ordinary skill in the art will now appreciate that, under appropriate circumstances, considering such issues as design preference, user preferences, marketing preferences, cost, structural requirements, available materials, technological advances, etc., other means for securing an elastic band to the sleeve such as, for example, adhesive, integral manufacture, etc., may suffice.

Following the insertion of right arm 201 into right inner restraining sleeve 206 and the insertion of left arm into left restraining inner-sleeve 207, medical garment 102 is preferably wrapped around torso 106 of gown wearer 104 and fastened to gown wearer 104. Such fastening preferably further restrains right arm 201 and left arm 202 of gown wearer 104 from reaching each other such arm and assists keeping the gown wearer 104 from flailing such arms. Preferred means for fastening medical garment 102 to gown wearer 104 is by fasteners, preferably, a set of paired, preferably fabric, ties 138, as shown. Preferably, fabric ties 138 are fastened using bow-tie configuration 130, as shown in both FIG. 1 and FIG. 2. Fabric ties are preferred to provide a garment that can be worn for certain diagnostic devices such as X-ray, MRI and CAT scans, wherein a metal-free garment is preferable or required. Upon reading this specification, those with ordinary skill in the art will now appreciate that, under appropriate circumstances, considering such issues as design preference, user preferences, marketing preferences, cost, structural requirements, available materials, technological advances, etc., other tie arrangements such as, for example, half-knot, full-knot, slip-knot, etc., may suffice.

Medical garment 102 is preferably fastened in at least four different locations across torso 106 of gown wearer 104. These four tying locations preferably comprise: upper tie 122, lower tie 124, upper middle tie 126, and lower middle tie 128, as shown. Upper tie 122 is preferably separated by distance D1 (see FIG. 3 for "D" distance illustration)) of about 9 inches from upper middle tie 126. Upper middle tie 126 is preferably separated by distance D2 of about 9 inches from lower middle tie 128. Lower middle tie 128 is preferably separated by distance D3 of about 9 inches from lower tie 124. Lower tie 124 is preferably threaded through the entire bottom end portion 144 in such manner as to permit cinching of bottom end portion 144 onto gown wearer 104.

Preferably, hand 220 of gown wearer 104 preferably can protrude slightly through one of the about 9 inch openings between ties 138. Protrusion of hand 220 provides for gown wearer 104 to preferably hold a family member's hand for comfort and consoling as well as provide another portion for receiving medical treatment.

Medical garment 102 has concealed slit 118 with a preferable length of about 8 inches, preferably located at elbow portion 218. Concealed slit 118 (at least embodying herein wherein such medical garment system comprises access means for accessing at least one arm portion of the at least one gown wearer) is preferably manufactured in identical locations and dimensions on both exterior wrap portion 146 and preferably on the garment elbow portion 150 (about the middle of each respective right arm 201 and left arm 202) of right inner restraining sleeve 206 and left restraining inner-sleeve 207 (this arrangement at least embodies herein wherein such access means comprises such arm restrainer means). Concealed slit 118, when in use, permits medical personnel to have rapid access to elbow portion 218 of gown wearer 104 when gown wearer 104 requires medical treatment, such as, for example, IV maintenance, administering a shot, etc. The above-described arrangement at least embodies herein wherein such access means comprises medical-procedure-permitter means for permitting medical procedures relating to the at least one gown wearer.

Medical garment 102 is preferably designed to extend from about the level of neck 110 to at least slightly below buttocks of gown wearer 104 (preferably covering the entire torso). Preferably, medical garment 102 does not cover head 114 of user 104; rather, medical garment 102 provides an opening 115 for the passage of the head of gown wearer 104.

The above described use of the medical garment at least embodying herein a method used to administer at least one medical procedure to at least one patient's arm comprising the steps of: providing at least one torso enclosure, having at least one interior surface and at least one exterior surface, structured and arranged to enclose such torso; wherein said at least one torso enclosure comprises at least one arm restrainer, located adjacent said at least one interior surface, adapted to restrain the at least one arm of the at least one gown wearer; wherein said medical garment system comprises at least one access to access at least one arm portion of the at least one gown wearer; wherein said at least one access comprises said at least one arm restrainer; and wherein said at least one access comprises at least one medical-procedure-permitter structured and arranged to permit medical procedures relating to the at least one gown wearer; inserting such at least one patient's arm into such at least one arm restrainer; closing such hospital gown so as to restrain arm movement of such patient while administering such at least one medical procedure; administering such at least one medical procedure by way of such at least one access.

FIG. 3 shows a front perspective view illustrating medical garment 102, of medical garment system 100, unstitched and laid flat, according to the preferred embodiment of the present invention. Medical garment 102 preferably comprises multiple manufactured sizes to accommodate differing body sizes of the user. Thus, medical garment 102 comprises a range of preferred dimensions related to each of the differing manufactured sizes. These manufactured sizes preferably comprise at least a small size, a medium size, and a large size. In addition, preferred embodiments preferably comprise compact sizes to accommodate young children along with extra-large sizes for adult bariatric patients.

Medical garment 102 preferably comprises three panel sections. These three sections are identified herein as rear panel 302, left front panel 304, and right front panel 306, as shown. Rear panel 302 preferably comprises right end 308 and left end 310. Preferably, right end 308 of rear panel 302 is preferably curved convexly to produce rear panel upper right edge 330. Preferably, left end 310 of rear upper panel 302 is also preferably curved convexly to produce rear panel upper left edge 332.

Preferably, right front panel 306 comprises two ends identified herein as left interior end 312 and right exterior end 316. Preferably, left interior end 312 is preferably curved convexly to produce right panel upper left edge 334. Preferably, right panel upper right edge 338 is beveled as to preferably not constrain medical garment 102 around neck 110 of gown wearer 104.

Left front panel 304 comprises two ends which are: right interior end 314 and left exterior end 318. Right interior end 314 is preferably curved convexly to produce left panel upper right edge 336. Preferably, left panel upper right edge 340 is beveled as to preferably not constrain medical garment 102 around neck 110 of gown wearer 104.

FIG. 3 shows medical garment 102 laid flat, and unstitched; however, when medical garment is manufactured, right panel upper left edge 334 is preferably sewn to rear upper right edge 330 to create a right shoulder portion as preferably configured when medical garment 102 is in the preferred assembled configuration of FIG. 1 and FIG. 2. Moreover, left panel upper right edge 336 is preferably sewn to rear upper left edge 332 to create a left shoulder portion as preferably configured when medical garment 102 is in the preferred assembled configuration of FIG. 1 and FIG. 2.

Medical garment is preferably manufactured by stitching rear panel 302 to both left front panel 304 and right front panel 306. Rear panel 302 is sewn to left front panel 304, preferably by grasping together left end 310 of rear panel 302 and right interior end 314 of left front panel 304. First seam 320 is preferably sewn with about a ½-inch overlap between rear panel 302 and left front panel 304. Left inner restraining sleeve 207 is preferably sewn into first seam 320, as shown.

Rear panel 302 is preferably sewn to right front panel 306, preferably by grasping together right end 308 of rear panel 302 and left interior end 312 of right front panel 306. Second seam 322 is preferably sewn with about a ½-inch overlap between rear panel 302 and right front panel 306, as shown. Right inner restraining sleeve 206 is preferably sewn into second seam 322, as shown.

Left fastening elements 324 are preferably located on left exterior end 318 of left front panel 304, as shown. Left fastening elements 324 preferably comprise first upper fastening element 326A, first upper middle fastening element 326B, first lower middle fastening element 326C, and first lower fastening element 326D. Left fastening elements 324 are preferably about 18 inches in length. As stated above, left fastening elements 324 are preferably equally spaced, preferably comprising at about 9 inches apart, as shown in FIG. 3.

Right fastening elements 327 are preferably located on right exterior end 316 of right front panel 306, as shown. Right fastening elements 327 preferably comprise second upper fastening element 328A, second upper middle fastening element 328B, second lower middle fastening element 328C, and first lower fastening element 328D. Right fastening elements 327 are preferably about 18 inches in length. As previously stated, right fastening elements 327 are preferably equally spaced at about 9-inches apart, as shown in FIG. 3.

Left fastening elements 324 preferably mate with right fastening elements 327 to preferably close medical garment 102 in a secure manner, as shown in FIG. 1.

Medical garment 102 is preferable manufactured using at least one flexible, resilient, washable, and readily disposable material, preferable cloth such as cotton, or synthetic fiber, such as polyester. Medical garment 102 is preferably constructed from a material that does not inhibit the passage of X-rays, and hence, does not need to be removed when gown wearer 104 requires an X-ray.

Those with ordinary skill in the art will now appreciate that upon reading this specification and by their understanding the art of sewing garments as described herein, methods of making the medical garment will be understood by those knowledgeable in such art.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A medical garment system, relating to restraining at least one arm adjacent the torso of a gown wearer, comprising a medical garment comprising:

a) at least one torso enclosure, having at least one interior surface and at least one exterior surface, structured and arranged to enclose such torso;

b) wherein said at least one torso enclosure comprises at least one arm restrainer, located adjacent said at least one interior surface, adapted to restrain the at least one arm of the gown wearer;

c) wherein said at least one arm restrainer comprises at least one access to access the upper arm portion of at least one arm of the gown wearer through said at least one exterior surface;

d) wherein said at least one arm restrainer is structured and arranged to limit movement of the at least one arm preventing the at least one arm, when restrained by said at least one arm restrainer, from reaching the upper arm portion of the other such at least one arm of the gown wearer;

e) wherein said at least one access comprises at least one medical-procedure-permitter structured and arranged to permit medical procedures relating to the gown wearer;

f) wherein, when restrained by said at least one arm restrainer, the at least one arm is prevented from reaching said at least one medical-procedure-permitter to impede such medical procedures; and g) wherein said at least one torso enclosure comprises at least one hospital gown h) wherein said at least one torso enclosure permits bipedal movement of the gown wearer's legs to allow for walking and movement in to and out of hospital beds;

i) wherein said at least one medical-procedure-permitter comprises
   i) at least one first aperture through said at least one arm restrainer, and
   ii) at least one second aperture through said at least one exterior surface;
   iii) wherein said at least one first aperture and said at least one second aperture are aligned;

j) wherein said at least one first aperture and said at least one second aperture are formed at least one seam of said at least one hospital gown.

2. The medical garment system according to claim 1, wherein said at least one arm restrainer comprises at least one right-arm-inner-restraining sleeve and at least one left-arm-inner-restraining sleeve.

3. The medical garment system according to claim 2, wherein said at least one right-arm-inner-restraining sleeve and said at least one left-arm-inner-restraining sleeve each further comprise at least one elastic cuff structured and arranged to assist maintaining the at least one arm within said at least one right-arm-inner-restraining sleeve and said at least one left-arm-inner-restraining sleeve when so placed.

4. The medical garment system according to claim 1, wherein said at least one hospital gown comprises one hospital gown comprising one first longitudinal end and one second longitudinal end structured and arrange to enclose at least the torso of the gown wearer.

5. The medical garment system according to claim 4, wherein said one hospital gown further comprises:
   a) at least one upper portion, at least one middle portion and at least one bottom portion; and
   b) at least one openable closure structured and arranged to assist in opening or closing said one first longitudinal end and one second longitudinal end;
   c) wherein when the arms of such gown wearer are placed into a respective said at least one right-arm-inner-restraining sleeve and said at least one left-arm-inner-restraining sleeve and said at least one hospital gown is closed with said at least one openable closure, the arms of the gown wearer are restrained from contact with each other.

6. The medical garment system according to claim 5, wherein said at least one openable closure comprises:
   a) at least four pair of ties, each said pair of ties situate opposite each other, structured and arranged to be tied together;
   b) wherein one of said at least four pair of ties is situate on said at least one upper portion of said one hospital gown;
   c) wherein two of said at least four pair of ties are situate about said at least one middle portion of said one hospital gown; and
   d) wherein one of said at least four pair of ties is situate on said at least one bottom portion of said one hospital gown.

7. The medical garment system according to claim 1, wherein said at least one first aperture and said at least one second aperture are situate adjacent about the center of said at least one arm restrainer.

8. A medical garment system, relating to restraining at least one arm adjacent the torso of a gown wearer, comprising:
   a) at least one torso enclosure, having at least one interior surface and at least one exterior surface, structured and arranged to enclose such torso;
   b) wherein said at least one torso enclosure comprises at least one arm restrainer, located adjacent said at least one interior surface, structured and arranged to restrain the at least one arm of the gown wearer;
   c) wherein said at least one arm restrainer comprises at least one access to access an upper arm portion of at least one arm of the gown wearer through said at least one exterior surface;
   d) wherein said at least one access comprises at least one medical-procedure-permitter structured and arranged to permit medical procedures relating to the gown wearer;
   e) wherein said at least one torso enclosure comprises at least one hospital gown permitting bipedal movement of the gown wearer's legs to allow for walking and movement in to and out of hospital beds;
   f) wherein said arm restrainer is structured and arranged to limit movement of the at least one arm preventing the at least one arm, when restrained by said at least one arm restrainer, from reaching the upper arm portion of the other such at least one arm of the gown wearer;
   g) wherein said at least one arm restrainer comprises one right-arm-inner-restraining sleeve and one left-arm-inner-restraining sleeve;
   h) wherein said at least one access comprises:
      i) at least one first aperture through said at least one arm restrainer,
      ii) at least one second aperture through said at least one exterior surface, and
      iii) wherein said at least one first aperture and said at least one second aperture are aligned;
   i) wherein, when restrained by said at least one arm restrainer, the at least one arm is prevented from reaching said at least one medical-procedure-permitter to impede such medical procedures; and
   j) wherein said at least one first aperture and said at least one second aperture are formed at least one seam of said at least one hospital gown.

9. The medical garment system according to claim 8 wherein said at least one first aperture and said at least one second aperture are situate adjacent about the center of said at least one arm restrainer.

10. The medical garment system according to claim 9 wherein said at least one right-arm-inner-restraining sleeve and said at least one left-arm-inner-restraining sleeve each further comprise at least one elastic cuff structured and arranged to assist maintaining the at least one arm within said at least one right-arm-inner-restraining sleeve and said at least one left-arm-inner-restraining sleeve when so placed.

11. A method of administering at least one medical procedure to at least one patient's arm comprising the steps of:
   a) providing at least one torso enclosure, having at least one interior surface and at least one exterior surface, structured and arranged to enclose a torso of a patient;
   b) wherein such at least one torso enclosure comprises a medical garment comprising at least one arm restrainer, located adjacent said at least one interior surface, adapted to restrain at least one arm of the patient preventing the at least one arm, when restrained by such at least one arm restrainer, from reaching the upper arm portion of the other such at least one arm of the patient;
   c) wherein such at least one arm restrainer comprises at least one access to access the upper arm portion at least one arm of the patient through such at least one exterior surface;
   d) wherein such at least one access comprises at least one medical-procedure-permitter structured and arranged to permit medical procedures relating to the patient;
   e) inserting the at least one arm of the patient into such at least one arm restrainer;
   f) closing such at least one torso enclosure so as to restrain arm movement of the patient, preventing the at least one arm, when restrained by such at least one arm restrainer, from reaching such at least one medical-procedure-permitter, while administering such at least one medical procedure; and
   g) administering such at least one medical procedure by way of such at least one access;
   h) wherein such at least one torso enclosure comprises at least one hospital gown;
   i) wherein, when restrained by such at least one arm restrainer, the at least one arm is prevented from reaching such at least one medical-procedure-permitter to impede such medical procedures;
   j) wherein such at least one torso enclosure permits bipedal movement of the gown wearer's legs to allow for walking and movement in to and out of hospital beds;
   k) wherein said at least one medical-procedure-permitter comprises
      i) at least one first aperture through such at least one arm restrainer, and
      ii) at least one second aperture through such at least one exterior surface;
      iii) wherein such at least one first aperture and such at least one second aperture are aligned; and
   l) wherein such at least one first aperture and such at least one second aperture are formed at least one seam of such at least one hospital gown.

12. The method of administering according to claim 11, wherein such at least one arm restrainer comprises at least one right-arm-inner-restraining sleeve and at least one left-arm-inner-restraining sleeve.

13. The method of administering according to claim 12, wherein such at least one right-arm-inner-restraining sleeve and such at least one left-arm-inner-restraining sleeve each further comprise at least one elastic cuff structured and arranged to assist maintaining the at least one arm within such at least one right-arm-inner-restraining sleeve and such at least one left-arm-inner-restraining sleeve when so placed.

14. The method of administering according to claim 13, wherein such at least one torso enclosure comprises:
   a) at least one upper portion, at least one middle portion and at least one bottom portion; and
   b) at least one openable closure structured and arranged to assist in opening or closing such at least one torso enclosure;
   c) wherein when the arms of the patient are placed into a respective such at least one right-arm-inner-restraining sleeve and such at least one left-arm-inner-restraining sleeve and such at least one torso enclosure is closed with such at least one openable closure, the arms of the patient are restrained from contact with each other.

15. A medical garment system, relating to restraining at least one arm of a gown wearer, comprising:
   a) torso enclosure means for enclosing the torso of the gown wearer;
   b) wherein said torso enclosure means comprises arm restrainer means for restraining the at least one arm of the gown wearer preventing the at least one arm, when restrained by said arm restrainer means, from reaching the upper arm portion of the other such at least one arm of the gown wearer;
   c) wherein said arm restrainer means comprises access means for accessing the upper arm portion of at least one arm of the gown wearer; and
   d) wherein said access means comprises medical-procedure-permitter means for permitting medical procedures relating to the gown wearer;
   e) wherein, when restrained by said arm restrainer means, the at least one arm is prevented from reaching said medical-procedure-permitter means to impede such medical procedure;
   wherein said torso enclosure means permits bipedal movement of the gown wearer's legs to allow for walking and movement in to and out of hospital beds;
   h) wherein said medical-procedure-permitter means comprises
      i) at least one first aperture through said arm restrainer means, and
      ii) at least one second aperture through said torso enclosure means;
      iii) wherein said at least one first aperture and said at least one second aperture are aligned; and
   i) wherein said at least one first aperture and said at least one second aperture are formed at least one seam of said at least one hospital gown.

* * * * *